United States Patent
Arisaka

(10) Patent No.: US 7,332,995 B2
(45) Date of Patent: Feb. 19, 2008

(54) CAPACITIVE HUMIDITY SENSOR AND METHOD FOR MANUFACTURING THE SAME

(75) Inventor: Naoki Arisaka, Kariya (JP)

(73) Assignee: DENSO CORPORATION, Kariya (JP)

( * ) Notice: Subject to any disclaimer, the term of this patent is extended or adjusted under 35 U.S.C. 154(b) by 139 days.

(21) Appl. No.: 11/376,212

(22) Filed: Mar. 16, 2006

(65) Prior Publication Data

US 2006/0238290 A1    Oct. 26, 2006

(30) Foreign Application Priority Data

Apr. 22, 2005    (JP)    ............... 2005-125570

(51) Int. Cl.
  *H01C 7/00*    (2006.01)
(52) U.S. Cl. ............... 338/35; 73/335.04; 361/523
(58) Field of Classification Search ............ 338/34–35; 73/335.04; 361/523, 528, 502–503, 509, 361/512
  See application file for complete search history.

(56) References Cited

U.S. PATENT DOCUMENTS

| | | | |
|---|---|---|---|
| 4,386,336 A * | 5/1983 | Kinomoto et al. ............ | 338/35 |
| 5,028,906 A * | 7/1991 | Moriya et al. ................ | 338/35 |
| 5,254,371 A * | 10/1993 | Hegner et al. ............... | 427/487 |
| 6,580,600 B2 | 6/2003 | Toyoda et al. | |
| 6,647,782 B2 * | 11/2003 | Toyoda ................... | 73/335.04 |
| 2002/0114125 A1 | 8/2002 | Toyoda et al. | |
| 2003/0094045 A1* | 5/2003 | Hamamoto et al. ...... | 73/335.04 |

FOREIGN PATENT DOCUMENTS

| | | |
|---|---|---|
| JP | A-06-118045 | 4/1994 |
| JP | A-08-264374 | 10/1996 |
| JP | A-2002-71612 | 3/2002 |
| JP | A-2005-114357 | 4/2005 |

* cited by examiner

*Primary Examiner*—K. Richard Lee
(74) *Attorney, Agent, or Firm*—Posz Law Group, PLC

(57) ABSTRACT

A capacitive humidity sensor includes: a humidity sensing element; a substrate; and an insulation film. The humidity sensing element includes a pair of comb-shape electrodes and a humidity sensitive film. The comb-shape electrodes are surrounded by a dam provided by a part of the insulation film. The insulation film on the comb-shape electrodes has a first height. The part of the insulation film on the dam has a second height higher than the first height. The humidity sensitive film has a height equal to or lower than the second height, and is disposed inside of the dam. The dam further includes a first ring pattern made of a same material as the comb-shape electrodes.

19 Claims, 4 Drawing Sheets

CAPACITIVE HUMIDITY SENSOR AND METHOD FOR MANUFACTURING THE SAME

CROSS REFERENCE TO RELATED APPLICATION

This application is based on Japanese Patent Application No. 2005-125570 filed on Apr. 22, 2005, the disclosure of which is incorporated herein by reference.

FIELD OF THE INVENTION

The present invention relates to a capacitive humidity sensor and a method for manufacturing a capacitive humidity sensor.

BACKGROUND OF THE INVENTION

A capacitive humidity sensor and a method for manufacturing a capacitive humidity sensor are disclosed in, for example, JP-A-243690, which corresponds to U.S. Pat. No. 6,580,600-B2 and US Patent Application Publication No. 2002/0114125-A1. The sensor includes a humidity sensing element, a capacitance of which changes with humidity. The sensor 90 is shown in FIG. 4. The sensor 90 includes a humidity sensitive portion 30 and a circuit portion 40, which are disposed on one side of a semiconductor substrate 1.

The humidity sensitive portion 30 is composed of a pair of electrodes 91a, 91b, a silicon oxide film 2, a silicon nitride film 3 and a humidity sensitive film 4. The silicon oxide film 2 is formed on the substrate 1. The electrodes 91a, 91b face each other, are disposed on the silicon oxide film 2, and are separated each other. The silicon nitride film 3 and the humidity sensitive film 4 are formed to cover the electrodes 91a, 91b. The humidity sensitive film 4 is made of material, dielectric constant of which changes in accordance with humidity change of atmosphere. Accordingly, a capacitance between the electrodes 91a, 91b in the humidity sensitive portion 30 changes in accordance with the humidity change of the atmosphere around the sensor 90.

The circuit portion 40 controls and drives, i.e., energizes the humidity sensing element 10 in the humidity sensitive portion 30. The circuit portion 40 includes a reference capacitance portion 42 and a CMOS transistor portion 41. The reference capacitance portion 42 provides a reference capacitance, and the CMOS transistor portion 41 includes a CMOS transistor and the like. The capacitance change between the electrodes 91a, 91b in the humidity sensitive portion 30 is compared with the reference capacitance of the reference capacitance portion 42, so that a result of the comparison is processed in the CMOS transistor portion 41. Thus, the sensor 90 measures the capacitance change between the electrodes 91a, 91b in accordance with the humidity change so that the humidity of the atmosphere is detected.

The humidity sensitive film 4 in the above sensor 90 is manufactured by a screen printing method. Thus, the manufacturing cost of the sensor 90 becomes low. However, the humidity sensitive film 4 formed by the screen printing method has following problems.

The material for providing the humidity sensitive film 4 is firstly mixed into a paste. Then, the paste is printed by the screen printing method. However, the humidity sensitive film 4 formed by the screen printing method has variation of viscosity in each part and variation of printing pressure in each part. Thus, saddle phenomenon may be occurred, as shown in FIG. 6. The saddle phenomenon is such that a thickness of a center of the humidity sensitive film 4 is different from a thickness of a periphery of the humidity sensitive film 4 after the humidity sensitive film 4 is printed.

When the saddle phenomenon is occurred in the humidity sensitive film 4 in the sensing element 10, the characteristics of the sensor 90 may be varied. Thus, detection accuracy of the humidity is reduced.

SUMMARY OF THE INVENTION

In view of the above-described problem, it is an object of the present invention to provide a capacitive humidity sensor having high detection accuracy. It is another object of the present invention to provide a method for manufacturing a capacitive humidity sensor having high detection accuracy.

A capacitive humidity sensor includes: a humidity sensing element, a capacitance of which is changeable in accordance with humidity so that the humidity sensing element detects the humidity; a substrate, on which the humidity sensing element is disposed; and an insulation film disposed on the substrate. The humidity sensing element includes a pair of comb-shape electrodes and a humidity sensitive film. The comb-shape electrodes are interleaved so that the comb-shape electrodes face together. The comb-shape electrodes are disposed on the substrate. The humidity sensitive film covers the comb-shape electrodes through the insulation film. The humidity sensitive film has dielectric constant, which is changeable in accordance with the humidity. The comb-shape electrodes are surrounded by a dam, which is provided by a part of the insulation film. The insulation film disposed on the comb-shape electrodes has a first height from the substrate. The part of the insulation film disposed on the dam has a second height from the substrate, the second height being higher than the first height. The humidity sensitive film has a height equal to or lower than the second height. The humidity sensitive film is disposed inside of the dam. The dam further includes a first ring pattern so that the first ring pattern surrounds the comb-shape electrode and the humidity sensitive film, the first ring pattern which is made of a same material as the comb-shape electrode.

In the above sensor, the humidity sensitive film having homogeneous film thickness is easily formed by pouring the material of the humidity sensitive film into the inside of the dam. Thus, the saddle phenomenon is prevented from occurring in the humidity sensitive film. Thus, the thickness of the humidity sensitive film becomes uniform; and therefore, the detection accuracy of the sensor is improved. Further, the first ring pattern is made of the same material as the comb-shape electrode. Accordingly, the manufacturing cost of the sensor is suppressed so that the total cost of the sensor is reduced.

Alternatively, the first ring pattern may have a thickness substantially equal to a thickness of the comb-shape electrode. Alternatively, the sensor further includes a reference capacitor having a reference capacitance. The reference capacitance has small humidity dependency, which is smaller than that of the humidity sensing element. The reference capacitor includes at least one poly silicon electrode. The dam further includes a second ring pattern so that the second ring pattern surrounds the comb-shape electrode and the humidity sensitive film. The second ring pattern is made of poly silicon. Further, the second ring pattern may have a thickness substantially equal to a thickness of the poly silicon electrode of the reference capacitor. Alternatively, the reference capacitor further includes a second poly silicon electrode. The dam further includes a third ring pattern so that the third ring pattern surrounds the comb-shape electrode and the humidity sensitive film. The third ring pattern is made of poly silicon. Further, the third ring pattern may have a thickness substantially equal to a thickness of the second poly silicon electrode of the reference capacitor.

Further, a capacitive humidity sensor includes: a humidity sensing element, a capacitance of which is changeable in accordance with humidity so that the humidity sensing element detects the humidity; a substrate, on which the humidity sensing element is disposed; and an insulation film disposed on the substrate. The humidity sensing element includes a pair of comb-shape electrodes and a humidity sensitive film. The comb-shape electrodes are interleaved so that the comb-shape electrodes face together. The comb-shape electrodes are disposed on the substrate. The humidity sensitive film covers the comb-shape electrodes through the insulation film. The humidity sensitive film has dielectric constant, which is changeable in accordance with the humidity. The comb-shape electrodes are surrounded by a dam. The insulation film disposed on the comb-shape electrodes has a first height from the substrate. The dam has a second height from the substrate, the second height being higher than the first height. The humidity sensitive film has a height equal to or lower than the second height. The humidity sensitive film is disposed inside of the dam.

In the above sensor, the dam can be formed of any material, in general. Further, the humidity sensitive film having homogeneous film thickness is easily formed by pouring the material of the humidity sensitive film into the inside of the dam. Thus, the saddle phenomenon is prevented from occurring in the humidity sensitive film. Thus, the thickness of the humidity sensitive film becomes uniform; and therefore, the detection accuracy of the sensor is improved.

Alternatively, the sensor further may include a circuit portion for controlling the humidity sensing element. The substrate is made of semiconductor material. The circuit portion is disposed on the substrate at a position apart from the humidity sensing element. The dam includes a ring pattern so that the ring pattern surrounds the comb-shape electrode and the humidity sensitive film. The ring pattern is made of a same material as an electrode or a wiring in the circuit portion. Further, the ring pattern may have a thickness substantially equal to a thickness of the electrode or the wiring in the circuit portion.

Further, a method for manufacturing a capacitive humidity sensor includes the steps of: forming a humidity sensing element on a substrate, a capacitance of the humidity sensing element being changeable in accordance with humidity so that the humidity sensing element detects the humidity, wherein the humidity sensing element includes a pair of comb-shape electrodes and a humidity sensitive film, the comb-shape electrodes are interleaved so that the comb-shape electrodes face together, the comb-shape electrodes are disposed on the substrate, the humidity sensitive film covers the comb-shape electrodes through an insulation film, the insulation film is disposed on the substrate, and the humidity sensitive film has dielectric constant, which is changeable in accordance with the humidity; and forming a dam provided by a part of the insulation film, wherein the comb-shape electrodes are surrounded by the dam, the insulation film disposed on the comb-shape electrodes has a first height from the substrate, and the part of the insulation film disposed on the dam has a second height from the substrate, the second height being higher than the first height. The step of forming the humidity sensing element includes the steps of: forming the comb-shape electrodes on the substrate; and pouring material of the humidity sensitive film to an inside of the dam so that the humidity sensitive film has a height equal to or lower than the second height. The dam further includes a first ring pattern so that the first ring pattern surrounds the comb-shape electrode. The first ring pattern is made of a same material as the comb-shape electrode. In the step of forming the comb-shape electrodes, the first ring pattern is formed together with the comb-shape electrodes.

The above method provides the sensor as follows. The humidity sensitive film having homogeneous film thickness is easily formed by pouring the material of the humidity sensitive film into the inside of the dam. Thus, the saddle phenomenon is prevented from occurring in the humidity sensitive film. Thus, the thickness of the humidity sensitive film becomes uniform; and therefore, the detection accuracy of the sensor is improved. Further, the first ring pattern is made of the same material as the comb-shape electrode. Accordingly, the manufacturing cost of the sensor is suppressed so that the total cost of the sensor is reduced.

Alternatively, the method may further include the step of: forming a reference capacitor having a reference capacitance on the substrate. The reference capacitance has small humidity dependency, which is smaller than that of the humidity sensing element. The reference capacitor includes at least one poly silicon electrode. The dam further includes a second ring pattern so that the second ring pattern surrounds the comb-shape electrode. The second ring pattern is made of poly silicon. The step of forming the reference capacitor includes the step of forming the poly silicon electrode in the reference capacitor. In the step of forming the poly silicon electrode of the reference capacitor, the second ring pattern is formed together with the poly silicon electrode.

Alternatively, the reference capacitor may further include a second poly silicon electrode. The dam further includes a third ring pattern so that the third ring pattern surrounds the comb-shape electrode. The third ring pattern is made of poly silicon. The step of forming the reference capacitor further includes the step of forming the second poly silicon electrode in the reference capacitor. In the step of forming the second poly silicon electrode of the reference capacitor, the third ring pattern is formed together with the second poly silicon electrode.

Further, a method for manufacturing a capacitive humidity sensor includes the steps of: forming a humidity sensing element on a substrate, a capacitance of which is changeable in accordance with humidity so that the humidity sensing element detects the humidity, wherein the humidity sensing element includes a pair of comb-shape electrodes and a humidity sensitive film, the comb-shape electrodes are interleaved so that the comb-shape electrodes face together, the comb-shape electrodes are disposed on the substrate, the humidity sensitive film covers the comb-shape electrodes through an insulation film, the insulation film is disposed on the substrate, and the humidity sensitive film has dielectric constant, which is changeable in accordance with the humidity; and forming a dam in such a manner that the dam surrounds the comb-shape electrodes, wherein the insulation film disposed on the comb-shape electrodes has a first height from the substrate, and the dam has a second height from the substrate, the second height being higher than the first height. The step of forming the humidity sensing element includes the steps of: forming the comb-shape electrodes on the substrate; and pouring material of the humidity sensitive film to an inside of the dam so that the humidity sensitive film has a height equal to or lower than the second height.

The above method provides the sensor as follows. In the sensor, the dam can be formed of any material, in general. Further, the humidity sensitive film having homogeneous film thickness is easily formed by pouring the material of the humidity sensitive film into the inside of the dam. Thus, the saddle phenomenon is prevented from occurring in the humidity sensitive film. Thus, the thickness of the humidity sensitive film becomes uniform; and therefore, the detection accuracy of the sensor is improved.

Alternatively, the method may further include the step of: forming a circuit portion on the substrate at a position apart from the humidity sensing element. The circuit portion controls the humidity sensing element. The substrate is made of semiconductor material. The dam includes a ring pattern so that the ring pattern surrounds the comb-shape electrodes. The ring pattern is made of a same material as an electrode or a wiring in the circuit portion. The step of forming the circuit portion includes the step of forming the electrode or the wiring in the circuit portion. In the step of forming the electrode or the wiring in the circuit portion, the ring pattern is formed together with the electrode or the wiring.

BRIEF DESCRIPTION OF THE DRAWINGS

The above and other objects, features and advantages of the present invention will become more apparent from the following detailed description made with reference to the accompanying drawings. In the drawings.

DETAILED DESCRIPTION OF THE PREFERRED EMBODIMENT

Figure 4:
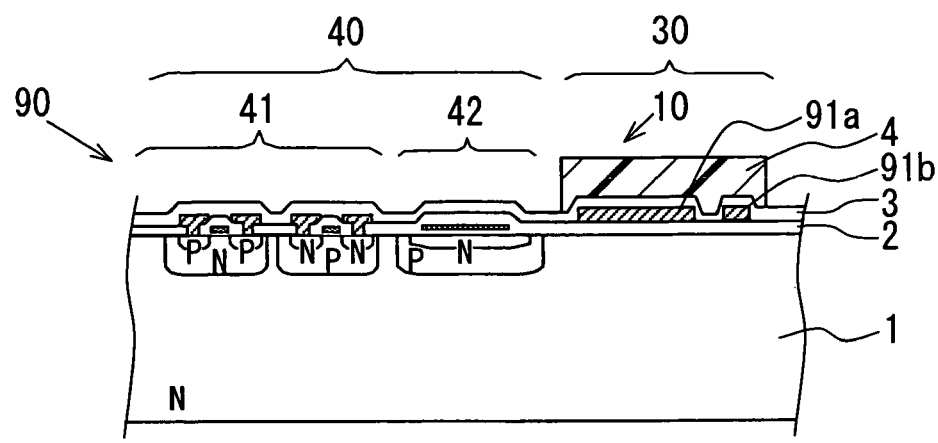
FIG. 4 is a partial cross sectional view showing a main part of a capacitive humidity sensor according to a prior art.
Figure 6:
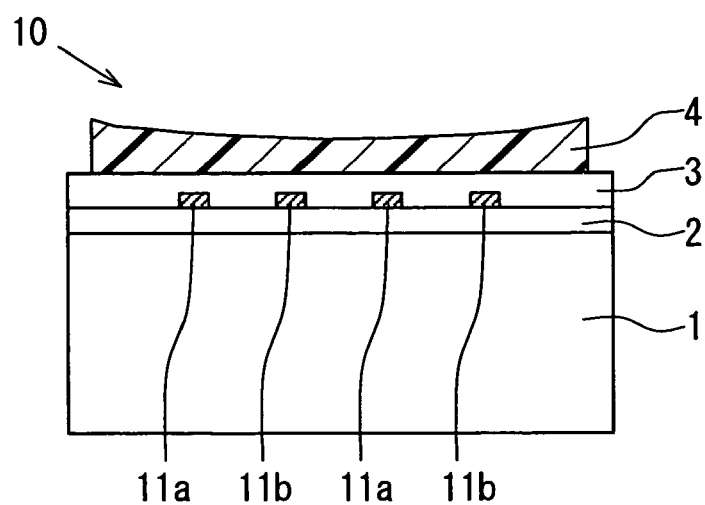
FIG. 6 is a schematic cross sectional view showing a humidity sensitive film formed by a screen printing method, according to the prior art.
Figure 5A:
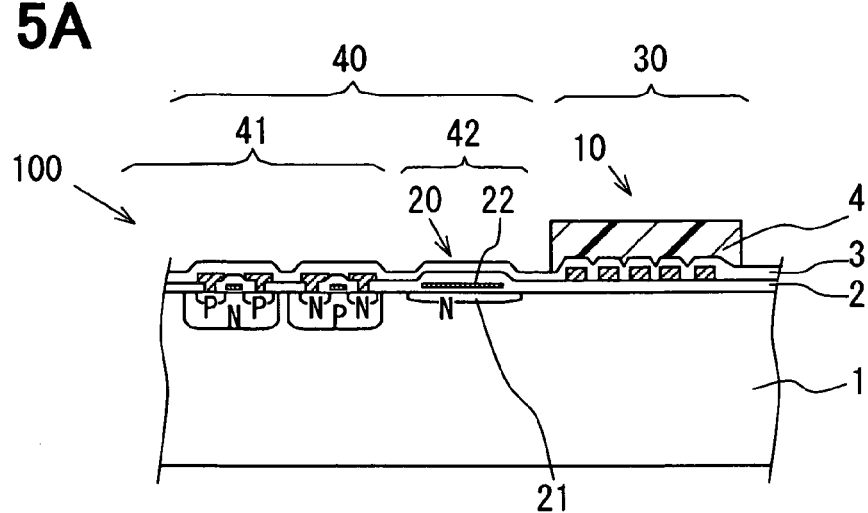
FIG. 5A is a partial cross sectional view showing a main part of a capacitive humidity sensor according to a comparison of the preferred embodiment.
Figure 5B:
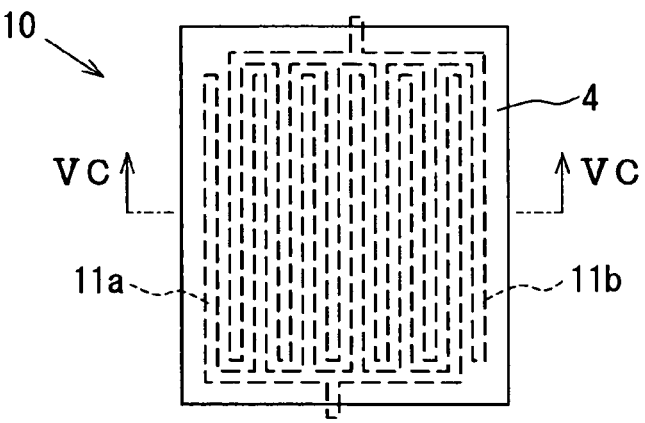
FIG. 5B is a top view showing the capacitive humidity sensor.
Figure 5C:
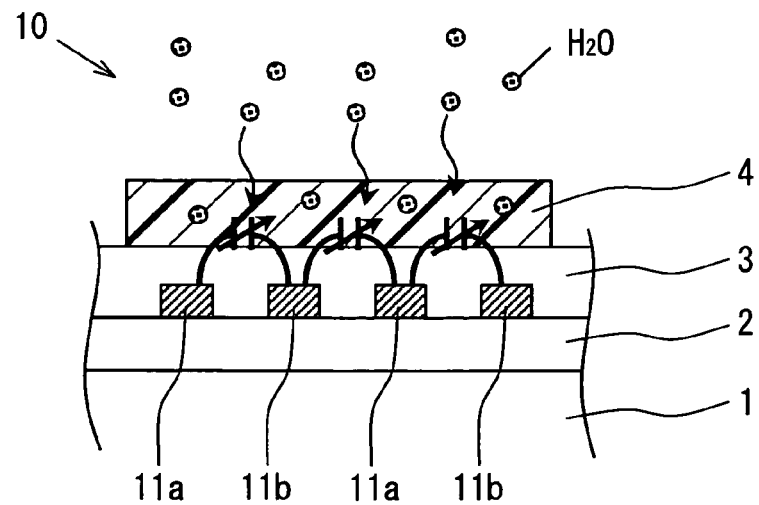
FIG. 5C is a cross sectional view showing the sensor taken along line VC-VC in FIG. 5B.

The inventor has preliminarily studied about a capacitive humidity sensor. FIGS. 5A to 5C show the capacitive humidity sensor 100 as a comparison of a preferred embodiment of the present invention. The sensor 100 includes the humidity sensitive portion 30 having a humidity sensing element 10 and the circuit portion 40, which are formed on the same side of the substrate 1. The substrate 1 is made of silicon. The circuit portion 40 for driving the humidity sensing element 10includes the reference capacitance portion 42 having a reference capacitor 20 and the CMOS transistor portion 41. The electrode shape of the humidity sensitive portion 30 in FIG. 5A is different from that in FIG. 4.

The humidity sensing element 10 includes a pair of comb-shape electrodes 11a, 11b, which is disposed on the same plane of the substrate 1. Further, a comb tooth of one of the comb-shape electrodes 11a, 11b separately faces a comb tooth of the other one of the comb-shape electrodes 11a, 11b so that the comb teeth of the electrodes 11a, 11b are interleaved each other. Thus, the humidity sensing element 10 is a comb-teeth electrode type capacitive element. The comb-shape electrode 11a, 11b is made of a wiring material such as aluminum. The comb-shape electrode 11a, 11b is formed on the silicon oxide film 2. The capacitance of the humidity sensing element 10 having the comb-shape electrodes 11a, 11b in FIG. 5B is larger than that of the humidity sensing element having a pair of the electrodes 91a, 91b in FIG. 4. Further, the manufacturing process of the comb-shape electrode type humidity sensing element 10 is more simple than that of the parallel plate type humidity sensing element with a pair of the electrodes 91a, 91b having a parallel plate construction. Therefore, the comb-shape electrode type humidity sensing element 10 can be reliably manufactured by a conventional semiconductor process. Further, the manufacturing cost of the comb-shape electrode type humidity sensing element 10 becomes smaller so that the total cost of the sensor 100 becomes small.

The humidity sensitive film 4 is formed on the comb-shape electrodes 11a, 11b through the silicon nitride film 3 as an insulation protection film so that the comb-shape electrodes 11a, 11b are covered with the humidity sensitive film 4. The dielectric constant of the humidity sensitive film 4 is changeable in accordance with humidity. The humidity sensitive film 4 is made of poly-imide resin, and the relative permittivity of the humidity sensitive film 4 is in a range between 3 and 4. Here, the water, i.e., $H_2O$, has the relative permittivity of 80. Accordingly, when the water, i.e., a $H_2O$ molecule, adheres to humidity sensitive film 4, the dielectric constant of the humidity sensitive film 4 becomes larger. Thus, the capacitance of the sensing element 10 is increased. Therefore, the sensing element 10 detects the humidity on the basis of the capacitance change of the element 10 in accordance with change of the dielectric constant of the humidity sensitive film 4, which is changeable in accordance with the humidity of the atmosphere around the element 10.

The reference capacitor 20 in the sensor 100 shown in FIG. 5A includes the silicon oxide film 2 as dielectric substance, a N type diffusion layer 21 and a poly silicon layer 22. The N type diffusion layer 21 and the poly silicon layer 22 are formed on the semiconductor substrate 1, and work as an electrode so that the capacitor 20 provides a parallel plate type capacitance element. Specifically, the silicon oxide film 2 is sandwiched between the N type diffusion layer 21 and the poly silicon layer 22, which provide two electrodes of the reference capacitor 20. The reference capacitor 20 has no humidity sensitive film 4; and therefore, the reference capacitance of the reference capacitor 20 does not change even when the humidity of the atmosphere around the reference capacitance portion 42 changes.

The capacitance change of the sensing element 10 in accordance with the humidity change of the atmosphere is compared with the reference capacitance of the reference capacitor 20. Then, a comparison result is processed in the CMOS transistor portion 41 so that the sensor detects the humidity of the atmosphere around the sensing element 10.

The humidity sensitive film 4 in the above sensor 100 is manufactured by a screen printing method. Thus, the manufacturing cost of the sensor 100 becomes low. However, the humidity sensitive film 4 formed by the screen printing method has following problems.

The material for providing the humidity sensitive film 4 is firstly mixed into a paste having viscosity of about 50 Pa·s. Then, the paste is printed by the screen printing method. However, the humidity sensitive film 4 formed by the screen printing method has variation of viscosity in each part and variation of printing pressure in each part. Thus, saddle phenomenon may be occurred. When the saddle phenomenon is occurred in the humidity sensitive film 4 in the sensing element 10, the characteristics of the sensor 100 may be varied. Thus, detection accuracy of the humidity is reduced.

Figure 1A:
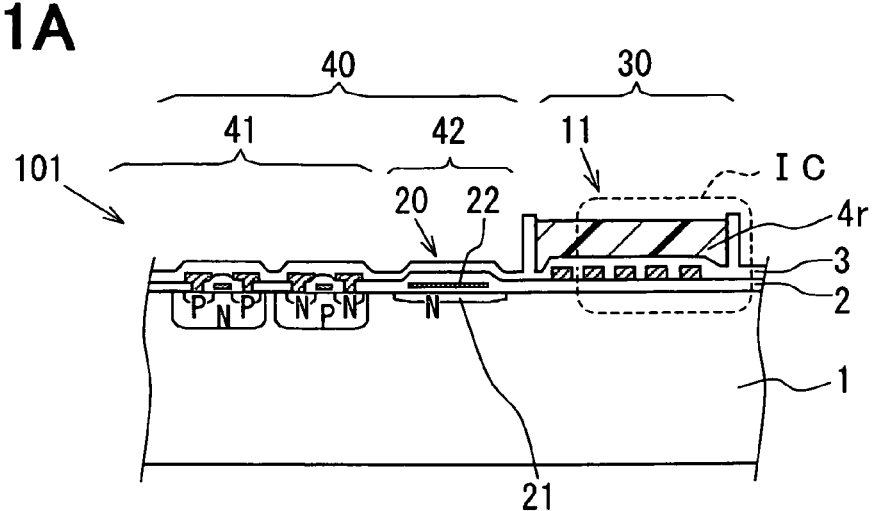
FIG. 1A is a partial cross sectional view showing a main part of a capacitive humidity sensor according to a preferred embodiment of the present invention.
Figure 1B:
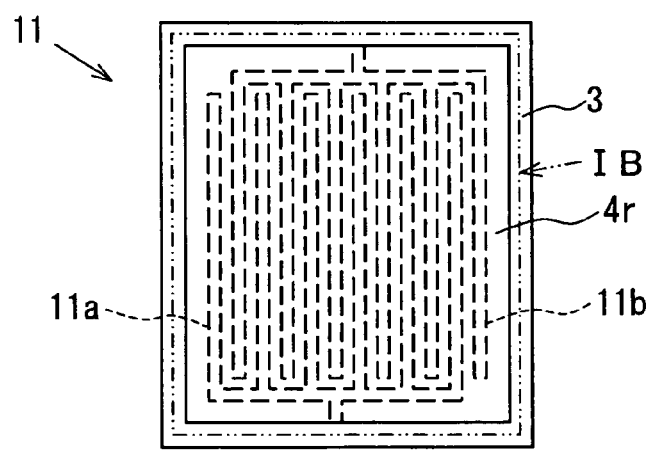
FIG. 1B is a top view showing the capacitive humidity sensor.
Figure 1C:
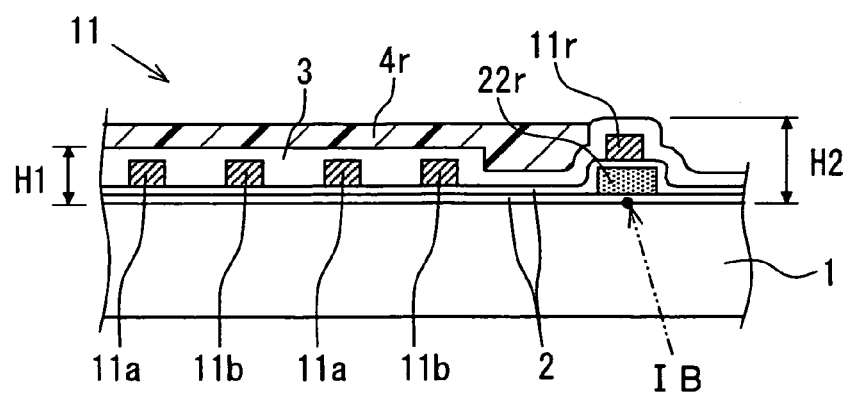
FIG. 1C is a partially enlarged cross sectional view showing a part IC of the sensor in FIG. 1A.

In view of the above problem, a capacitive humidity sensor 101 according to a preferred embodiment of the present invention shown in FIGS. 1A to 1C is presented. The sensor 101 includes a humidity sensing element 11, capacitance of which is changeable in accordance with humidity of atmosphere around the sensing element 11. The sensor 101 includes a humidity sensitive portion 30 and a circuit portion 40. The humidity sensitive portion 30 has the sensing element 11. The circuit portion 40 drives and controls the sensing element 11. The circuit portion 40 includes a CMOS transistor portion 41 and a reference capacitance portion 42. The humidity sensitive portion 30 and the circuit portion 40 are disposed on one side of a semiconductor substrate 1. The reference capacitance portion 42 includes a reference capacitor 20.

The construction of the humidity sensitive portion 30 in the sensor 101 in FIG. 1A is different from that in the sensor 100 in FIG. 5A. The humidity sensing element 11 in the sensor 101 is a comb-shape capacitance element. The element 11 includes a pair of comb-shape electrodes 11a, 11b and a humidity sensitive film 4r, which are disposed on a semiconductor substrate 1. The electrodes 11a, 11b are separated each other, and face each other so that the comb teeth of the electrodes 11a, 11b are interleaved each other. The humidity sensitive film 4r is formed on the substrate 1 through the silicon nitride film 3 as an insulation film 3 to cover the electrodes 11a, 11b. The dielectric constant of the humidity sensitive film 4r is changeable in accordance with the humidity. The electrodes 11a, 11b are made of wiring material such as aluminum, and disposed on a silicon oxide film 2. The insulation film 3 is made of silicon nitride film, and the humidity sensitive film 4r is made of poly-imide resin.

In FIG. 1C, H1 represents a surface height of the insulation film 3 from the surface of the substrate 1. Specifically, the height H1 is defined as the height of a part of the insulation film 3 disposed on the electrodes 11a, 11b. H2 represents a surface height of the insulation film 3 from the surface of the substrate 1. Specifically, the height H2 is defined as the height of another part of the insulation film 3 disposed on a chain double-dashed line, which defines an area IB shown in FIG. 1B. The area IB surrounds the electrodes 11a, 11b. The height H2 is set to be higher than the height H1. The humidity sensitive film 4r is formed inside of the area IB in such a manner that the height of the humidity sensitive film 4r is equal to or lower than the height H2.

Accordingly, the insulation film 3 provides a dam construction. The dam is provided by the part of the insulation film 3, two ring patterns 11r, 22r and a part of the silicon oxide film 2. Therefore, when the humidity sensitive film 4r is formed, the substrate 1 is placed on a horizontal table as a reference table so that the material of the humidity sensitive film 4r having low viscosity is poured into the inside of the area IB by a predetermined amount. Thus, the humidity sensitive film 4r having constant thickness is formed on the substrate 1, i.e., the thickness of the humidity sensitive film 4r becomes homogeneous.

Here, preferably, the viscosity of the material of the humidity sensitive film 4r is equal to or smaller than 10 Pa·s. In this case, after the material of the humidity sensitive film 4r is poured into the inside of the area IB, solvent in a paste of the material of the humidity sensitive film 4r is removed with placing the substrate 1 on the horizontal table so that the constant thickness of the humidity sensitive film 4r is obtained easily.

In the humidity sensitive film 4r formed by the above pouring method, the saddle phenomenon is prevented from occurring in the film 4r. Accordingly, the thickness of the humidity sensitive film 4r covering the electrodes 11a, 11b becomes uniform, i.e., homogeneous. Thus, the detection accuracy of the sensor 101 is improved.

In the sensor 101, to form the dam construction, the sensor 101 includes two ring patterns 22r, 11r. The ring patterns 11r, 22r are disposed on the substrate to surround the electrodes 11a, 11b. Specifically, the ring patterns 11r, 22r are disposed on the chain double-dashed line of IB. The ring pattern 22r is made of poly silicon film, which is the same material as an electrode 22, i.e., the poly silicon layer of the reference capacitor 20. The electrode 22 of the reference capacitor 20 is one of electrodes in the capacitor 20. Accordingly, the ring pattern 22r is formed simultaneously together with the electrode 22 of the reference capacitor 20. The ring pattern 11r is made of aluminum or the like, which is the same material as the comb-shape electrodes 11a, 11b. Thus, the ring pattern 11r is formed simultaneously together with the comb-shape electrode 11a, 11b. Specifically, the forming step of the ring pattern 22r is the same as the forming step of the electrode 22 of the reference capacitor 20, and the forming step of the ring pattern 11r is the same as the forming step of the comb-shape electrode 11a, 11b.

By forming the ring pattern 11r, the thickness of a part of the insulation film 3 disposed on the electrodes 11a, 11b is set to be equal to the thickness of another part of the insulation film 3 disposed on the ring pattern 11r. Specifically, by forming the ring pattern 11r, it is easy to increase the height H2 of the insulation film 3 disposed on the chain double-dashed line shown as IB in FIG. 1B. Further, by forming the ring pattern 22r, the height H2 of the insulation film 3 on the chain double-dashed line of IB is set to be higher by the thickness of the ring pattern 22r than the height H1 of the insulation film 3 on the comb-shape electrode 11a, 11b. Here, the thickness of the ring pattern 22r is the same as the electrode 22 of the reference capacitor 20. Thus, an additional new step for forming the ring patterns 11r, 22r is not necessary, since the ring patterns 11r, 22r can be formed together with the comb-shape electrodes 11a, 11b and the electrode 22 of the reference capacitor 20, respectively. Specifically, the ring patterns 11r, 22r can be formed only by changing a mask pattern in a case where the comb-shape electrodes 11a, 11b and the electrode 22 of the reference capacitor 20 are formed, respectively. Accordingly, the manufacturing cost of the sensor 101 is reduced.

In general, in a case where a capacitive humidity sensor having a circuit portion such as the sensor 101 shown in FIG. 1A, a protection gel for protecting the circuit portion is applied on the circuit portion. In the sensor 101, the protection gel is prevented from introducing into the inside of the area IB since the insulation film 3 on the chain double-dashed line of IB has the sufficient height H2, which protects the gel from flowing onto the humidity sensitive film 4r. Thus, the dam prevents the gel from entering into the inside of the area IB.

(Modifications)

Figure 2A:
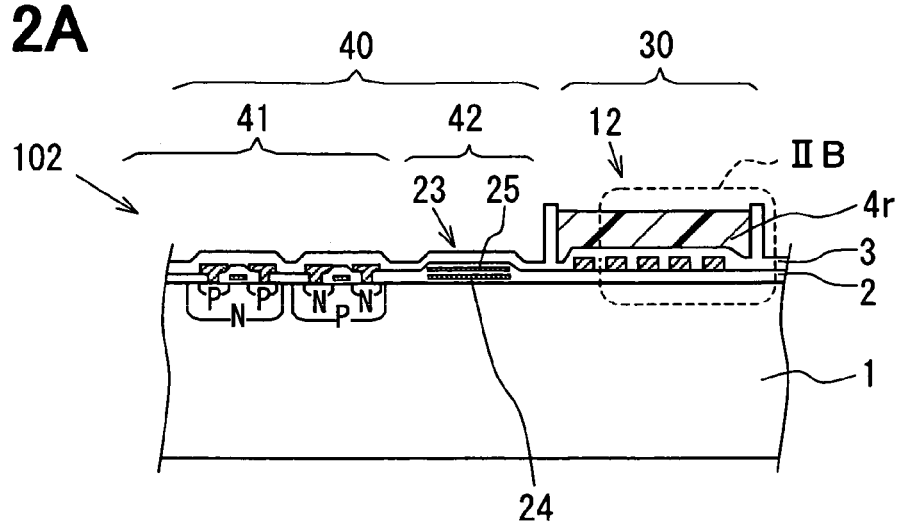
FIG. 2A is a partial cross sectional view showing a main part of a capacitive humidity sensor according to a modification of the preferred embodiment of the present invention.
Figure 2B:
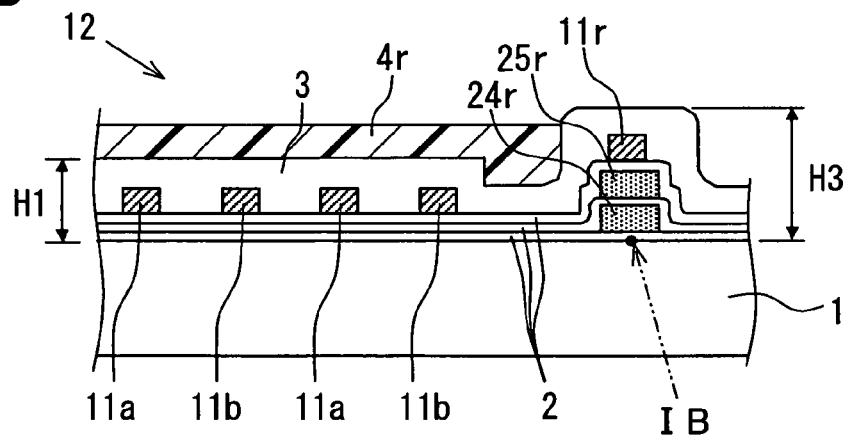
FIG. 2B is a partially enlarged cross sectional view showing a part IIB of the sensor in FIG. 2A.

FIGS. 2A and 2B show another capacitive humidity sensor 102 according to a modification of the preferred embodiment. The sensor 102 includes the reference capacitor 23 in the reference capacitance portion 42 and the humidity sensing element 12 in the humidity sensitive portion 30. Although the reference capacitor 20 shown in FIG. 1A has the N type diffusion layer 21 as the lower electrode and the poly silicon layer 22 as the upper electrode, the reference capacitor 23 shown in FIG. 2A includes two poly silicon layers 24, 25 as the upper and the lower electrodes. The humidity sensitive portion 30 includes three ring patterns 11r, 24r, 25r, as shown in FIG. 2B. The material of the ring pattern 11r is the same as the comb-shape electrodes 11a, 11b in the humidity sensing element 11. The material of the ring patterns 24r, 25r is the same as the upper and the lower electrodes 24, 25 in the reference capacitor 23. The three ring patterns 11r, 24r, 25r and the insulation film 3 provide the area IB, i.e., the dam. The ring pattern 24r made of poly silicon film is formed together with the lower electrode 24 of the reference capacitor 23, and the ring pattern 25r made of poly silicon film is formed together with the upper electrode 25 of the reference capacitor 23. The ring pattern 11r is formed together with the comb-shape electrodes 11a, 11b. Specifically, the forming steps of the ring patterns 24r, 25r are the same as the forming steps of the electrodes 24, 25 of the reference capacitor 23, respectively, and the forming step of the ring pattern 11r is the same as the forming step of the comb-shape electrode 11a, 11b.

By forming two ring patterns 24r, 25r, the height H3 of the insulation film 3 disposed on the chain double-dashed line shown as IB in FIG. 2B becomes higher than the height H2 in FIG. 1C. Thus, the thickness of the humidity sensitive film 4r in the area IB can be controlled with high design degree of freedom.

Although the ring patterns 22r, 24r, 25r are formed simultaneously together with the electrodes 22, 24, 25 of the reference capacitor 20, 23, the ring patterns 22r, 24r, 25r may be formed simultaneously together with other electrodes and/or other wirings in the circuit portion 40. Specifically, when the circuit portion 40 is formed on the substrate 1 at a position apart from the humidity sensing element 11, 12, the ring patterns 22r, 24r, 25r may be formed from the same material as the other electrodes and/or the other wirings in the circuit portion 40. Thus, the forming steps of the ring patterns 22r, 24r, 25r are the same as the forming steps of the other electrodes and/or the other wirings in the circuit portion 40. Accordingly, the manufacturing cost of the sensor 101, 102 is reduced.

Figure 3:
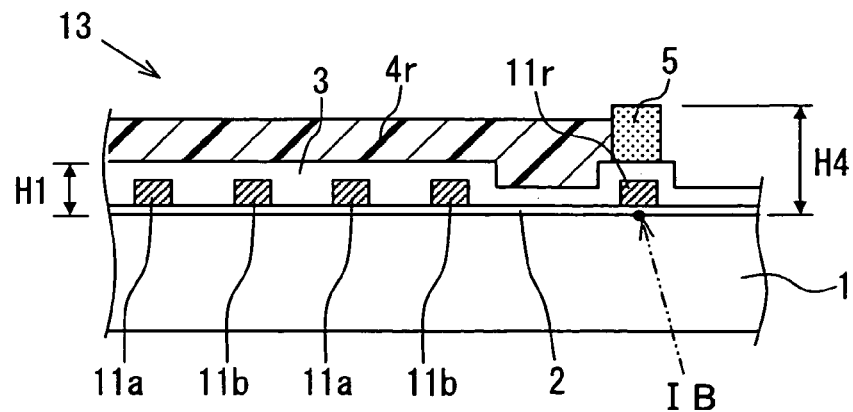
FIG. 3 is a partially enlarged cross sectional view showing a part of a capacitive humidity sensor according to another modification of the preferred embodiment of the present invention.

FIG. 3 shows further another capacitive humidity sensor according to a second modification of the preferred embodiment. The sensor includes a humidity sensing element 13. The humidity sensing element 13 has the dam construction provided by a ring pattern 5. Specifically, the height H4 of the ring pattern 5 disposed on the chain double-dashed line shown as IB in FIG. 3B is set to be higher by the thickness of the ring pattern 5 than the height H1 of the insulation film 3 disposed on the comb-shape electrode 11a, 11b. The humidity sensitive film 4r is formed in the area IB in such a manner that the height of the humidity sensitive film 4r is lower than the height H4 of the ring pattern 5.

Thus, by using the ring pattern 5 made of any material, the height H4 of the ring pattern 5 becomes higher than the height H1 of the insulation film 3 so that the dam construction is formed. Accordingly, the humidity sensitive film 4r having the constant thickness in the area IB can be formed, i.e., the thickness of the humidity sensitive film 4r becomes homogeneous. The humidity sensitive film 4r can be formed by the pouring method so that the saddle phenomenon is prevented from occurring in the film 4r. Accordingly, the thickness of the humidity sensitive film 4r covering the electrodes 11a, 11b becomes uniform. Thus, the detection accuracy of the sensor 101 is improved.

Although the humidity sensitive portion 30 and the circuit portion 40 are formed on the same substrate 1, a capacitive humidity sensor having a humidity sensing element only formed on a substrate may include the dam construction.

While the invention has been described with reference to preferred embodiments thereof, it is to be understood that the invention is not limited to the preferred embodiments and constructions. The invention is intended to cover various modification and equivalent arrangements. In addition, while the various combinations and configurations, which are preferred, other combinations and configurations, including more, less or only a single element, are also within the spirit and scope of the invention.

What is claimed is:

1. A capacitive humidity sensor comprising:
 a humidity sensing element, a capacitance of which is changeable in accordance with humidity so that the humidity sensing element detects the humidity;
 a substrate, on which the humidity sensing element is disposed; and
 an insulation film disposed on the substrate, wherein
 the humidity sensing element includes a pair of comb-shape electrodes and a humidity sensitive film,
 the comb-shape electrodes are interleaved so that the comb-shape electrodes face together,
 the comb-shape electrodes are disposed on the substrate,
 the humidity sensitive film covers the comb-shape electrodes through the insulation film,
 the humidity sensitive film has dielectric constant, which is changeable in accordance with the humidity,
 the comb-shape electrodes are surrounded by a dam, which is provided by a part of the insulation film,
 the insulation film disposed on the comb-shape electrodes has a first height from the substrate,
 the part of the insulation film disposed on the dam has a second height from the substrate, the second height being higher than the first height,
 the humidity sensitive film has a height equal to or lower than the second height,
 the humidity sensitive film is disposed inside of the dam, and
 the dam further includes a first ring pattern so that the first ring pattern surrounds the comb-shape electrodes and the humidity sensitive film, the first ring pattern which is made of a same material as the comb-shape electrodes.

2. The sensor according to claim 1, wherein
 the first ring pattern has a thickness substantially equal to a thickness of the comb-shape electrodes.

3. The sensor according to claim 1, further comprising:
 a reference capacitor having a reference capacitance, wherein
 the reference capacitance has small humidity dependency, which is smaller than that of the humidity sensing element,
 the reference capacitor includes at least one poly silicon electrode,
 the dam further includes a second ring pattern so that the second ring pattern surrounds the comb-shape electrodes and the humidity sensitive film, and
 the second ring pattern is made of poly silicon.

4. The sensor according to claim 3, wherein
 the second ring pattern has a thickness substantially equal to a thickness of the poly silicon electrode of the reference capacitor.

5. The sensor according to claim 3, wherein
 the reference capacitor further includes a second poly silicon electrode,
 the dam further includes a third ring pattern so that the third ring pattern surrounds the comb-shape electrodes and the humidity sensitive film, and
 the third ring pattern is made of poly silicon.

6. The sensor according to claim 5, wherein
 the third ring pattern has a thickness substantially equal to a thickness of the second poly silicon electrode of the reference capacitor.

7. A capacitive humidity sensor comprising:
a humidity sensing element, a capacitance of which is changeable in accordance with humidity so that the humidity sensing element detects the humidity;
a substrate, on which the humidity sensing element is disposed; and
an insulation film disposed on the substrate, wherein
the humidity sensing element includes a pair of comb-shape electrodes and a humidity sensitive film,
the comb-shape electrodes are interleaved so that the comb-shape electrodes face together,
the comb-shape electrodes are disposed on the substrate,
the humidity sensitive film covers the comb-shape electrodes through the insulation film,
the humidity sensitive film has dielectric constant, which is changeable in accordance with the humidity,
the comb-shape electrodes-are surrounded by a dam,
the insulation film disposed on the comb-shape electrodes has a first height from the substrate,
the dam has a second height from the substrate, the second height being higher than the first height,
the humidity sensitive film has a height equal to or lower than the second height, and
the humidity sensitive film is disposed inside of the dam.

8. The sensor according to claim 7, further comprising:
a circuit portion for controlling the humidity sensing element, wherein
the substrate is made of semiconductor material,
the circuit portion is disposed on the substrate at a position apart from the humidity sensing element,
the dam includes a ring pattern so that the ring pattern surrounds the comb-shape electrodes and the humidity sensitive film, and
the ring pattern is made of a same material as an electrode or a wiring in the circuit portion.

9. The sensor according to claim 8, wherein
the ring pattern has a thickness substantially equal to a thickness of the electrode or the wiring in the circuit portion.

10. A method for manufacturing a capacitive humidity sensor comprising the steps of:
forming a humidity sensing element on a substrate, a capacitance of the humidity sensing element being changeable in accordance with humidity so that the humidity sensing element detects the humidity, wherein the humidity sensing element includes a pair of comb-shape electrodes and a humidity sensitive film, the comb-shape electrodes are interleaved so that the comb-shape electrodes face together, the comb-shape electrodes are disposed on the substrate, the humidity sensitive film covers the comb-shape electrodes through an insulation film, the insulation film is disposed on the substrate, and the humidity sensitive film has dielectric constant, which is changeable in accordance with the humidity; and
forming a dam provided by a part of the insulation film, wherein the comb-shape electrodes are surrounded by the dam, the insulation film disposed on the comb-shape electrodes has a first height from the substrate, and the part of the insulation film disposed on the dam has a second height from the substrate, the second height being higher than the first height, wherein
the step of forming the humidity sensing element includes the steps of:
forming the comb-shape electrodes on the substrate; and
pouring material of the humidity sensitive film to an inside of the dam so that the humidity sensitive film has a height equal to or lower than the second height,
the dam further includes a first ring pattern so that the first ring pattern surrounds the comb-shape electrodes,
the first ring pattern is made of a same material as the comb-shape electrodes, and
in the step of forming the comb-shape electrodes, the first ring pattern is formed together with the comb-shape electrodes.

11. The method according to claim 10, wherein
the first ring pattern has a thickness substantially equal to a thickness of the comb-shape electrodes.

12. The method according to claim 10, wherein
the material of the humidity sensitive film has viscosity equal to or smaller than 10 Pa·s.

13. The method according to claim 10, further comprising the step of:
forming a reference capacitor having a reference capacitance on the substrate, wherein
the reference capacitance has small humidity dependency, which is smaller than that of the humidity sensing element,
the reference capacitor includes at least one poly silicon electrode,
the dam further includes a second ring pattern so that the second ring pattern surrounds the comb-shape electrodes,
the second ring pattern is made of poly silicon,
the step of forming the reference capacitor includes the step of forming the poly silicon electrode in the reference capacitor, and
in the step of forming the poly silicon electrode of the reference capacitor, the second ring pattern is formed together with the poly silicon electrode.

14. The method according to claim 13, wherein
the second ring pattern has a thickness substantially equal to a thickness of the poly silicon electrode of the reference capacitor.

15. The method according to claim 13, wherein
the reference capacitor further includes a second poly silicon electrode,
the dam further includes a third ring pattern so that the third ring pattern surrounds the comb-shape electrodes,
the third ring pattern is made of poly silicon,
the step of forming the reference capacitor further includes the step of forming the second poly silicon electrode in the reference capacitor, and
in the step of forming the second poly silicon electrode of the reference capacitor, the third ring pattern is formed together with the second poly silicon electrode.

16. The method according to claim 15, wherein
the third ring pattern has a thickness substantially equal to a thickness of the second poly silicon electrode of the reference capacitor.

17. A method for manufacturing a capacitive humidity sensor comprising the steps of:
forming a humidity sensing element on a substrate, a capacitance of which is changeable in accordance with humidity so that the humidity sensing element detects the humidity, wherein the humidity sensing element includes a pair of comb-shape electrodes and a humidity sensitive film, the comb-shape electrodes are interleaved so that the comb-shape electrodes face together, the comb-shape electrodes are disposed on the substrate, the humidity sensitive film covers the comb-shape electrodes through an insulation film, the insulation film is disposed on the substrate, and the humidity sensitive film has dielectric constant, which is changeable in accordance with the humidity; and forming a dam in such a manner that the dam surrounds the comb-shape electrodes, wherein the insulation film disposed on the comb-shape electrodes has a first height from the substrate, and the dam has a second height from the substrate, the second height being higher than the first height, wherein the step of forming the humidity sensing element includes the steps of:
 forming the comb-shape electrodes on the substrate; and
 pouring material of the humidity sensitive film to an inside of the dam so that the humidity sensitive film has a height equal to or lower than the second height.

18. The method according to claim 17, further comprising the step of:
 forming a circuit portion on the substrate at a position apart from the humidity sensing element, wherein the circuit portion controls the humidity sensing element, the substrate is made of semiconductor material, the dam includes a ring pattern so that the ring pattern surrounds the comb-shape electrodes, the ring pattern is made of a same material as an electrode or a wiring in the circuit portion, the step of forming the circuit portion includes the step of forming the electrode or the wiring in the circuit portion, and in the step of forming the electrode or the wiring in the circuit portion, the ring pattern is formed together with the electrode or the wiring.

19. The method according to claim 18, wherein the ring pattern has a thickness substantially equal to a thickness of the electrode or the wiring in the circuit portion.

* * * * *